(12) United States Patent
Hirai et al.

(10) Patent No.: US 7,090,966 B2
(45) Date of Patent: Aug. 15, 2006

(54) PROCESS OF SURFACE TREATMENT, SURFACE TREATING DEVICE, SURFACE TREATED PLATE, AND ELECTRO-OPTIC DEVICE, AND ELECTRONIC EQUIPMENT

(75) Inventors: Toshimitsu Hirai, Chino (JP); Hironori Hasei, Okaya (JP)

(73) Assignee: Seiko Epson Corporation, (JP)

( * ) Notice: Subject to any disclaimer, the term of this patent is extended or adjusted under 35 U.S.C. 154(b) by 59 days.

(21) Appl. No.: 10/809,201

(22) Filed: Mar. 25, 2004

(65) Prior Publication Data
US 2004/0265506 A1 Dec. 30, 2004

(30) Foreign Application Priority Data
Mar. 26, 2003 (JP) ............................. 2003-085538
Feb. 12, 2004 (JP) ............................. 2004-035082

(51) Int. Cl.
*G03F 7/00* (2006.01)
(52) U.S. Cl. ...................................... 430/320; 430/397

(58) Field of Classification Search ................. 430/320, 430/397
See application file for complete search history.

(56) References Cited

U.S. PATENT DOCUMENTS

| 5,132,248 A | | 7/1992 | Drummond et al. ........ 505/325 |
| 6,451,386 B1 | * | 9/2002 | Simonetti .................... 427/512 |
| 6,861,377 B1 | * | 3/2005 | Hirai et al. .................. 438/781 |
| 2002/0001776 A1 | * | 1/2002 | Mori et al. ................. 430/302 |

* cited by examiner

*Primary Examiner*—Nicole Barreca
(74) *Attorney, Agent, or Firm*—Harness, Dickey & Pierce, P.L.C.

(57) ABSTRACT

A process of providing a hydrophobic property to the surface of a plate, and a process of providing a hydrophilic property to the surface by irradiating energy light (radiation) on the surface of the plate, which is provided with the hydrophobic property are provided. Variations in the accumulated illumination intensity of radiation on the surface of the plate are controlled to 20% or less.

5 Claims, 8 Drawing Sheets

PROCESS OF SURFACE TREATMENT, SURFACE TREATING DEVICE, SURFACE TREATED PLATE, AND ELECTRO-OPTIC DEVICE, AND ELECTRONIC EQUIPMENT

RELATED APPLICATIONS

This application claims priority to Japanese Patent Application No. 2003-085538 filed Mar. 26, 2003 and 2004-035082 filed Feb. 12, 2004 which are hereby expressly incorporated by reference herein in their entireties.

BACKGROUND

1. Technical Field

The present invention relates to a process of surface treatment, a surface treating device, a surface treated plate, an electro-optic device, and electronic equipment.

2. Background Art

Wiring used for electronic circuits or integrated circuits is manufactured, for example, by a photolithography method. In the photolithography method, the wiring is formed by applying photosensitive material called resist on a plate, on which a conductive film is applied in advance, developing by irradiating a circuit pattern, and etching the conductive film according to a resist pattern. The lithography method requires large scale equipment and complex processes such as a vacuum device, and the material usage efficiency is only several percent. Therefore, most of the material has to be put on the shelf, and hence it requires high manufacturing costs.

Alternatively, there is proposed a wiring pattern forming process using a process of discharging liquid drops, which is a so-called inkjet method, in which liquid material is discharged in the form of liquid drops from a liquid drop discharging head (For example, see U.S. Pat. No. 5,132, 248). In this method, ink for a wiring pattern, which is functional liquid containing conductive fine particles such as metal particles disposed therein is applied directly to the plate as a pattern, which is converted into a conductive film pattern by subsequently performing heat treatment or laser irradiation. This method has advantages such that photolithography is no longer necessary, and hence the process is significantly simplified, and at the same time, the amount of material to be used may be reduced.

In order to perform conductive film wiring by the inkjet method adequately, a process of selectively discharging liquid material by the inkjet method onto a liquid preferring (hydrophilic) portion of a plate, on which a pattern of a liquid rejecting portion (hydrophobic) and the liquid preferring portion is formed in advance, is proposed. In this case, since liquid containing the conductive fine particles dispersed therein tends to be trapped on the liquid preferring portion, formation of wiring with positional accuracy is achieved without forming a bank.

In this case, as a process of providing the hydrophobic property, a process of forming a liquid rejecting unimolecular film such as a self-organized film formed of an organic molecule on the surface of the plate, and a process of forming a fluorinated polymerized film on the surface of the plate, such as a plasma processing generating fluorocarbon contained compound as a reactive gas are known.

On the other hand, as a process of providing the hydrophilic property, a process of disrupting the liquid rejecting film once formed by irradiating ultraviolet light after liquid rejecting finishing is known.

However, there are problems as shown below.

In the case where a film pattern is formed using a plate on which the hydrophilic property or the hydrophobic property is provided, it is necessary to control the contact angle between the liquid member and the plate to be substantially uniform. This is because variations in hydrophilic property on the plate affect uniformity of dot diameter, that is, the line width or the film thickness.

However, in recent years, as the plate is upsized (enlarged), variations in hydrophilic property on the surface of the plate increase correspondingly. Therefore, there is fear that the contact angle between liquid and the plate cannot be controlled to be uniform.

In view of such points described above, it is an object of the present invention to provide a process of surface treatment in which the contact angle between the liquid member and the plate can be uniformly controlled even with the large size plate, a surface treating device, a surface treated plate, and an electro-optic device and electronic equipment having the surface treated plate.

SUMMARY

In order to achieve the above-described object, the present invention employs the following configuration.

A process of surface treatment of the present invention includes: a step of providing a hydrophobic property to the surface of a plate and a step of providing a hydrophilic property to the surface of the plate provided with the hydrophobic property by irradiating radiation (e.g., energy light) such as ultraviolet light, and is characterized in that variations in accumulated illumination intensity of the radiation on the surface of the plate are controlled to 20% or less. More preferably, variations in accumulated illumination intensity of the radiation on the surface of the plate are controlled to 15% or less.

Therefore, according to the present invention, variations in hydrophilic property provided on the plate can be control within a predetermined range, and variations in contact angle between the plate and liquid member can also be controlled. Consequently, the dot diameter of the liquid member applied on the plate, that is, uniformity of the line width or the film thickness formed of the liquid member is achieved.

As a process of controlling variations in accumulated illumination intensity of the radiation on the surface of the plate, a process of irradiating the radiation while relatively moving the plate with respect to a source of the radiation can be employed.

Accordingly, unevenness of distribution of energy to be irradiated on the plate can be alleviated and hence variations in accumulated illumination intensity can be controlled.

In the case where a plurality of rows of sources of the radiation are arranged in association with upsizing of the plate, it is preferred to move the plate in the direction of the arrangement of the plurality of radiation sources with respect thereto.

Consequently, according to the present invention, even when variations in irradiating energy exist among the plurality of sources, unevenness of distribution of the energy to be irradiated on the plate can be alleviated to obtain uniform accumulated illumination intensity.

Preferably, the present invention includes a step of measuring illumination intensity of the radiation at a plurality of points on the surface of the plate and in the vicinity of the plate respectively before providing the hydrophilic property, and a step of controlling irradiation of the radiation based on the accumulated illumination intensity of the radiation in the vicinity of the plate measured during the process of providing the hydrophilic property.

Consequently, according to the present invention, by obtaining the relative relation between the illumination intensity of the radiation on the surface of the plate and the illumination intensity of the radiation in the vicinity of the plate in advance, and then measuring and monitoring the illumination intensity of the radiation in the vicinity of the plate during the step of providing the hydrophilic property, the point at which accumulated illumination intensity of the radiation on the surface of the plate reaches a predetermined value can be detected without measuring the illumination intensity on the surface of the plate so that irradiation of the radiation can be stopped.

A surface treated plate according to the present invention is characterized in that the surface treatment is applied according to the above-described process of surface treatment.

Consequently, according to the present invention, since the desired hydrophilic property is provided uniformly, uniformity of the line width or the film thickness formed of the liquid member is achieved when the liquid member is discharged on the plate in the form of liquid drops.

An electro-optic device according to the present invention is characterized in that a conductive film wiring formed on the surface treated plate according to the present invention is provided. Electronic equipment of the present invention is characterized in that the electro-optic device according to the present invention is provided.

Consequently, according to the present invention, a high quality electro-optic device and electronic equipment which are advantageous for conduction of electricity and hardly suffers from defects such as disconnection or short circuit by virtue of the conductive film having a predetermined line width or film thickness.

On the other hand, a surface treating device of the present invention is a plate treating device for providing the surface with a hydrophilic property by irradiating the radiation on the surface of the plate, and is characterized in that a reciprocating device for relatively moving the source of the radiation and the plate.

Consequently, according to the present invention, unevenness of distribution of energy to be irradiated on the plate can be alleviated and hence variations in accumulated illumination intensity may be controlled.

Preferably, the plate is relatively moved along the direction of the arrangement of the plurality of rows of radiation sources.

Accordingly, in the case where a plurality of rows of sources for the radiation are arranged in association with upsizing of the plate, even when variations in irradiating energy exist among the plurality of radiation sources, unevenness of distribution of energy to be irradiated on the plate can be alleviated to obtain uniform accumulated illumination intensity.

DETAILED DESCRIPTION

Figure 1:
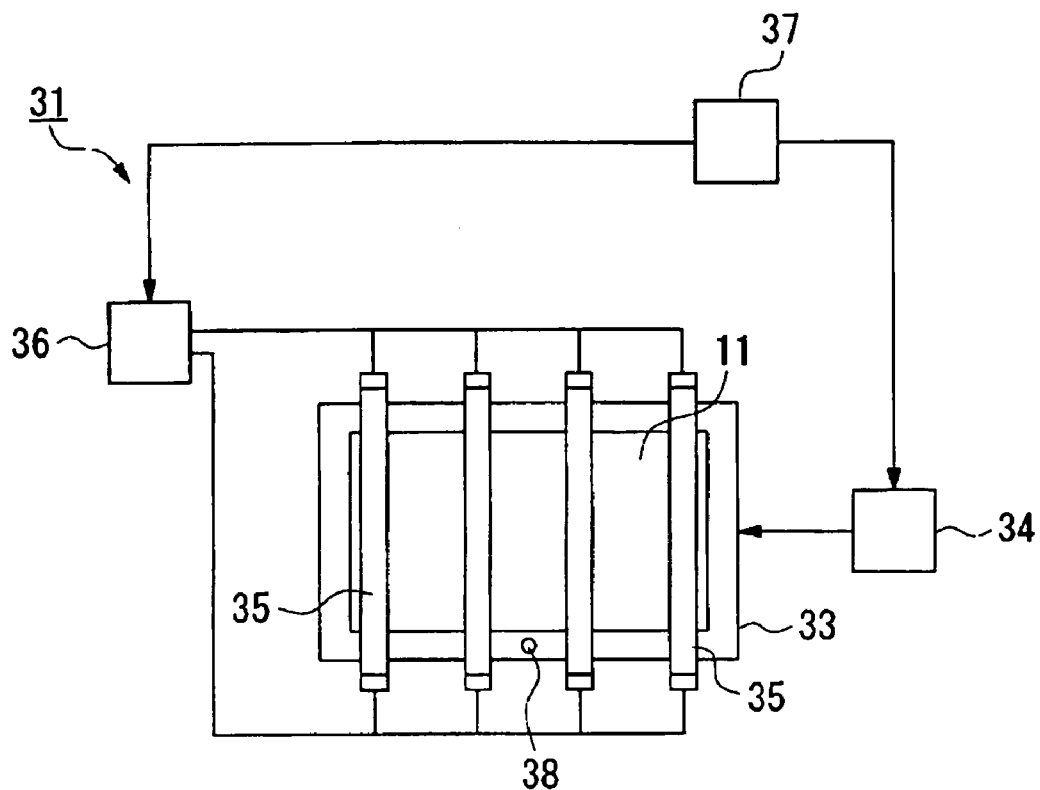
FIG. 1 is a general plan view showing a state in which a plate is placed on a surface treating device.

Referring to FIG. 1 to FIG. 10, embodiments of a process of surface treatment, a surface treating device, a surface treated plate, and an electro-optic device, and electronic equipment according to the present invention will be described.

FIRST EMBODIMENT

As a first embodiment, a process of surface treatment according to the present invention will be described.

The surface treatment according to the present embodiment is composed of a process of providing a hydrophobic property and a process of providing a hydrophilic property. Each of these processes will be described below.

Process of Providing Hydrophobic Property

As one of the processes of providing the hydrophobic property, there is a process of forming a self-organized film formed for example of an organic molecular film on the surface of a plate.

The organic molecular film for treating the surface of the plate includes a functional group which can be bonded to the plate at one end, a functional group for converting the property of the surface of the plate to a hydrophobic property or the like (controlling surface energy) at the other end, and a carbon straight chain or a partly branched carbon chain for connecting these functional groups, and is bonded to the plate and self-organized to form a molecular film, such as a unimolecular film.

The self-organized film includes a bonding function group capable of reacting to a foundation layer constituting an atom such as the plate and other straight molecules and is formed by orienting a chemical compound having an extremely high orientation by virtue of mutual action of the straight molecules. Since the self-organized film is formed by orienting a monomolecule, the film thickness can be reduced extremely. In addition, a uniform film in a molecular level is obtained. That is, since the same molecule is placed on the surface of the film, a uniform and superior hydrophobic property may be provided to the surface of the film.

For example, when fluoroalkylsilane is employed as the chemical compound having a high orientation, each compound is oriented so that the fluoroalkyl group is positioned on the surface of the film, and the self-organized film is formed. Therefore, a uniform hydrophobic property is provided on the surface of the film.

The compound which form such a self-organized film may be fluoroalkylsilane(hereinafter referred to as "FAS") such as Heptadecafluoro-1,1,2,2-tetrahydrodecyltriethoxysilane, Heptadecafluoro-1,1,2,2-tetrahydrodecyltrimethoxysilane, Heptadecafluoro-1,1,2,2-tetrahydrodecyltrichlorosilane, Tridecafluoro-1,1,2,2-tetrahydrooctyltriethoxysilane, Tridecafluoro-1,1,2,2- tetrahydrooctyltrimethoxysilane, Tridecafluoro-1,1,2,2-tetrahydrooctyltrichlorosilane, and Trifluoropropyltrimethoxysilane. As regards usage, though it is also preferable to use a single chemical compound independently, two or more chemical compounds may be combined for use as long as a desired object is not hindered. In the present invention, it is preferable to use the FAS as the chemical compound forming the self-organized film when considering the provision of adhesiveness with respect to the plate and a desirable hydrophobic property.

The FAS is generally represented by a constitutional formula $RnSiX_{(4-n)}$. Here, the sign n represents an integer between 1 and 3 inclusive, and X represents hydrolysable group such as methoxy group, ethoxy group, and halogen atom. The sign R represents fluoroalkyl group, having a constitution of $(CF_3)$ $(CF_2)$ x $(CH_2)$y (where the sign x represents an integer between 0 and 10 inclusive, and the sign y represents an integer between 0 and 4 inclusive), and when a plurality of Rs or Xs are bonded to Si, all the Rs or Xs may be the same, or may be different. The hydrolysable group represented by X forms silanol by hydrolysis, responds to hydroxyl group of the backing such as plate (glass, silicon) and bonded to the plate by siloxane bond. On the other hand, since R has a fluoro group such as $(CF_3)$ on the surface, it modifies the base surface such as the plate into a surface that does not get wet (low in surface energy).

The self-organized film formed of organic molecular film or the like is formed on the plate by placing the above-described material chemical and the plate in the same sealed container, and, in case of room temperature, leaving it to stand for about two or three days. Alternatively, by keeping the sealed container at a temperature of 100° C., it is formed in about three hours on the plate. While the process described above is a process for forming the self-organized film from the gas phase, it can also be formed from a liquid phase as well.

For example, the self-organized film can be formed on the plate by immersing the plate in a solution containing the material chemical compound and then cleaning and drying the same.

It is preferable to perform surface preparation by irradiating ultraviolet light onto the surface of the plate or by cleaning by solvent before forming the self-organized film.

As another process of providing the hydrophobic property, there is a process of irradiating plasma at a normal pressure or in vacuum.

The type of gas used for plasma treatment can be variously selected considering the quality of surface material of the plate. For example, fluorocarbon gas such as tetrafluromethane, perfluorohexane, or perfluorodecane can be used as a treatment gas. In this case, a film of polymer fluoride having a hydrophobic property can be formed on the surface of the plate.

The process of providing a hydrophobic property may also be performed by adhering a film having a desired hydrophobic property, such as a polyimide film applied with tetrafluromethane, on the surface of the plate. The polyimide film may be used as the plate as it is.

Process of providing a hydrophilic property

Since the surface of the plate in the stage in which the process of providing a hydrophobic property has finished usually has a hydrophobic property higher than the desired hydrophobic property, the hydrophobic property is alleviated by the process of providing a hydrophilic property.

As the process of providing a hydrophilic property, there is a process of irradiating ultraviolet light of 170–400 nm as radiation. With this process, the film having the hydrophobic property once formed can be partly destructed, but uniformly as a whole to alleviate the hydrophobic property.

In this case, the extent of alleviation of the hydrophobic property can be adjusted by the irradiation time of ultraviolet light, intensity, wavelength of the ultraviolet light, or the combination thereof. However, in the present embodiment, it is controlled by the accumulated illumination intensity of ultraviolet light on the surface of the plate, and variation of the accumulated illumination intensity is controlled to 20% or less.

Figure 2:
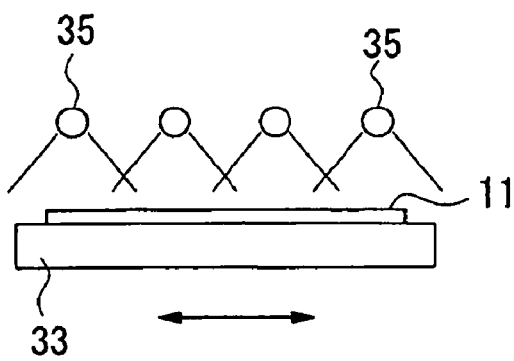
FIG. 2 is a front view of FIG. 1.

Referring now to FIG. 1 and FIG. 2, the surface treating device for providing the hydrophilic property to the surface of the plate will be described. FIG. 1 is a general plan view showing a state in which a plate 11 is placed on a surface treating device 31, and FIG. 2 is a front view.

The surface treating device 31 mainly includes a stage 33 capable of retaining the plate 11 and freely moving in the lateral direction in the drawing while retaining the plate, a driving unit 34 for driving the stage 33, a plurality of (four in this embodiment) mercury lamps (radiation source) 35 arranged above the stage 33 at regular intervals along the direction of movement of the stage 33, a switching unit 36 for switching on/off the irradiation of the mercury lamps 35, and a control unit 37 for controlling the driving unit 34 and the switching unit 36. The stage 33 is provided with an illumination intensity sensor 38 in the vicinity of the plate 11. The stage 33, the driving unit 34, and the control unit 37 constitute a moving device of the present invention.

Since irradiation energy of ultraviolet light at the end of the mercury lamp 35 is not stable (low) in comparison with the central portion thereof, the length thereof is determined so that the plate 11 is positioned in the area where stable irradiation energy can be obtained.

When performing the process of providing the hydrophilic property to the plate 11, the stage 33 which is retaining the plate 11 is reciprocated (swung, relatively moved) in the direction indicated by an arrow in FIG. 2 with respect to the mercury lamp 35 in a state in which the mercury lamp 35 is turned on under control of the control unit 37. The surface of the plate 11 obtains the hydrophilic property when the hydrophobic property is alleviated by ultraviolet light, for example, of 254 nm wavelength irradiated by the mercury lamp 35. In this case, when a plurality of mercury lamps 35 are used, slight variations in irradiation energy normally exist among the mercury lamps. However, since the plate 11 is moved via the stage 33, uneven distribution of energy irradiated to the plate can be alleviated.

On the other hand, before the process of providing the hydrophilic property, the relative relation among measurements is obtained by measuring the illumination intensity at a plurality of points (at least, the ends and the central point are included) on the surface of the plate by the illumination intensity sensor 38 on the test plate or the like in advance. Therefore, during the process of providing the hydrophilic property, the accumulated illumination intensity is monitored based on the illumination intensity measured by the illumination sensor 38, and the accumulated illumination intensity on the surface of the plate from the above-described relative relation and the result of monitoring is obtained. When the accumulated illumination intensity on the surface of the plate reaches the predetermined value, the control unit 37 stops irradiation of ultraviolet light via the switching unit 36. In this procedure, radiation can be irradiated to the surface of the plate at the predetermined accumulated illumination intensity without measuring the illumination intensity on the surface of the plate.

EXAMPLES

The result of measurement of accumulated illumination intensity on the surface of the plate, the dot diameter of liquid drops, and the contact angle during treatment of providing the hydrophilic property will be shown in Table 1. The result of measurement is obtained from liquid drops of silver(Ag)-independent dispersion liquid on the glass plate by irradiating ultraviolet light of 254 nm wavelength (illumination meter: Al ultraviolet light illumination meter UVPF-A1 PD254), and a target dot diameter is about 60 μm.

TABLE 1

| Accumulated illumination (mj/cm$^2$) | Dot diameter (diameter of liquid drop) | Contact angle (Ag-independent dispersion liquid) |
| --- | --- | --- |
| 1300 | 54 μm | 34° |
| 1400 | 60 μm | 31.6° |
| 1620 | 60 μm | 30° |
| 1800 | 61 μm | 29.4° |
| 1950 | 65 μm | 26° |

As shown in the result of the measurements, for example, when the accumulated illumination intensity 1620 mj/cm$^2$ is selected as a standard value, variations in dot diameter can be controlled to an extent in which no problems occurs in terms of the line width and the film thickness by irradiating ultraviolet light at the accumulated illumination intensity of 1300 mj/cm$^2$ (deviation from the standard value; about 20%) and at the accumulated illumination intensity of 1950 mj/cm$^2$ (deviation from the standard value; about 20%). Furthermore, the dot diameter, that is, the contact angle can be maintained substantially constant by irradiating ultraviolet light at the accumulated illumination intensity of 1400 mj/cm$^2$ (deviation from the standard value; about 14%) and at the accumulated illumination intensity of 1800 mj/cm$^2$ (deviation from the standard value; about 11%).

In this manner, according to the present embodiment, since the treatment of providing the hydrophilic property is performed based on variations in accumulated illumination intensity of ultraviolet light on the surface of the plate, further reliable control of the dot diameter and the contact angle on the plate surface is ensured. In addition, according to the present embodiment, variations in dot diameter and contact angle can be controlled by controlling variations in accumulated illumination intensity to 20% or less. In particular, by controlling variations in accumulated illumination intensity to 15% or less, the dot diameter, that is, the contact angle can be maintained constant, and hence uniformity of the line width of the film thickness formed by the liquid member is achieved.

Furthermore, in the present embodiment, even when irradiation energy varies among the plurality of mercury lamps, the effect of the variation can be alleviated and hence ultraviolet light can be irradiated onto the entire surface of the plate at a substantially uniform accumulated illumination intensity with a simple mechanism of moving the plate in the direction of the arrangement of the mercury lamps. In addition, according to the present embodiment, irradiation of the radiation on the surface of the plate at the predetermined accumulated illumination intensity is ensured without measuring the illumination intensity (accumulated illumination intensity) on the surface of the plate, since the relative relation among measurements is obtained by measuring the illumination intensity of the ultraviolet light at a plurality of points on the surface of the plate by the illumination intensity sensor 38 in advance, and then the accumulated illumination intensity is monitored based on the illumination intensity measured with the illumination intensity sensor 38.

SECOND EMBODIMENT

A wiring forming process, which is an example of a film pattern forming process with respect to the surface treated plate according to the present invention will be described as a second embodiment. The wiring forming process according to the present embodiment includes the process of surface treatment, a discharging process, and a process of heat treatment/optical treatment process. The respective processes will be described below.

Process of Surface Treatment

A plate on which conductive film wiring is to be formed may be of various types of material, such as Si wafer, quartz glass, glass, plastic film, or metal plate. Alternatively, the above-described materials formed with a semiconductor film, metal film, dielectric film, or organic film on the surface thereof as a foundation layer may be employed as the plate on which the conductive film wiring is to be formed.

The surface of the plate on which the conductive film wiring is to be formed is treated according to the process of the first embodiment, so that a predetermined contact angle with respect to liquid containing conductive fine particles indicates the desirable value.

The desired contact angle is selected as needed according to the step of discharging described later in detail. For example, the contact angle in the case where liquid drops are discharged over the liquid drops previously discharged in sequence is preferably between 30 [deg.] and 60 [deg.] inclusive. In addition, in a discharging process in which a plurality of liquid drops are discharged apart from each other so as not to come into contact with each other in the first discharging operation, and then the remaining portion is filled in the second and subsequent discharging operations, surface treatment with the contact angle of 60 [deg.] or larger, more preferably, between 90 [deg.] and 110 [deg.] inclusive is preferable.

Discharging Process

Subsequently, using a liquid drop discharging process, a liquid member containing conductive fine particles, which is material for forming conductive film wiring, is applied on the plate. As the liquid member containing the conductive fine particles, a dispersion liquid obtained by dispersing conductive fine particles in a dispersion medium is used.

For example, as conductive fine particles, oxide of the same, conductive polymer, and fine particles of superconductive polymer may be employed in addition to metal fine particles containing any one of gold, silver, copper, palladium, and nickel.

These conductive fine particles may be used by being coated with organic substance on the surface thereof in order to improve their dispersion property.

The diameter of the conductive fine particle is preferably between 5 nm and 0.1 μm inclusive. When it is larger than 0.1 μm, there is a risk that a nozzle of a liquid drop discharging head described later is clogged. In contrast, when it is smaller than 5 nm, the volume ratio of a coating agent with respect to the conductive fine particles increases, and hence the percentage of organic substance in the obtained film will be excessive.

The dispersion medium is not specifically limited as long as it can disperse the above-described conductive fine particles without generating cohesion. For example, in addition to water, alcohol such as methanol, ethanol, propanol, and butanol, hydrocarbon chemical compounds such as n-heptane, n-octane, decane, dodecane, tetradecane, toluen, xylene, cymene, durene, indene, dipentene, tetrahydronaphthalene, decahydronaphthalene, and cyclohexylbenzene, ether contained chemical compounds such as Ethylene glycol dimethyl ether, Ethylene glycol diethyl ether, Ethylene glycol methyl ethyl ether, Diethylene glycol dimethyl ether, Diethylene glycol diethyl ether, Diethylene glycol methyl ethyl ether, 1,2-Dimethoxyethane, Bis(2-methoxyethyl) ether, and p-Dioxane, and polar chemical compounds such as Propylene carbonate, γ-Butyrolactone, N-Methyl-2-pyrrolidone, Dimethylformamide, Dimethyl sulfoxide, and Cyclohexanone can be used. Among these media, water, alcohol group, hydrocarbon chemical compounds, ether containing chemical compound are preferable in terms of, dispersibility of fine particles and stability of dispersion liquid ease of application to the liquid drop discharging process (inkjet method), and more preferably, water and hydrocarbon chemical compounds are used as a dispersion medium.

The surface tension of dispersion liquid of conductive fine particles is preferably in the range between 0.02 N/m and 0.07 N/m inclusive. In the case where discharging liquid by the inkjet method, if the surface tension is below 0.02 N/m, wettability of the ink compound with respect to the nozzle surface increases, and hence deviation of flying direction is apt to occur. In contrast, if the surface tension exceeds 0.07 N/m, the amount of discharge and timing are difficult to control since the shape of meniscus at the extremity of the nozzle is not stable. In order to adjust the surface tension, it is recommended to add a slight amount of an agent such as fluorine contained-, silicone contained-, or nonionic- surface tension control agent substance to the dispersion liquid to the extent in which the contact angle with the plate is not considerably lowered. Nonionic surface tension control agent contributes to improve wettability of liquid with respect to the plate, improve a film leveling property, and prevent generation of fine roughness on the film. The above-described surface tension control agent may include organic chemical compounds such as alcohol, ether, ester, ketone as needed.

The viscosity of the above-described dispersion liquid is preferably between 1 mpa·s and 50 mpa·s inclusive. When discharging liquid material as liquid drops using the inkjet method, when the viscosity is smaller than 1 mpa·s, the portion around the nozzle is apt to be contaminated by ink flowing out therethrough, and when the viscosity is larger than 50 mPa·s, frequency of clogging of the nozzle hole increases, which hinders smooth discharge of liquid drops.

The discharging technology of the liquid drop discharging process includes an electrostatic control system, a pressure and vibration applying system, an electric-mechanic conversion system, an electric-thermal conversion system, and an electrostatic aspiration system. The electrostatic control system is a process of applying electric charge to the material via a charged electrode, and controlling the flying direction of material by a polarized electrode to allow the material to be discharged from the nozzle. The pressure and vibration applying system is a process of applying a super-high pressure about 30 kg/cm² to the material to allow the extremity of the nozzle to discharge the material. In this system, when the control voltage is not applied, the material is injected from the nozzle in a straight manner, and when the control voltage is applied, electrostatic repulsion occurs in the material so that the material is dispersed and hence is not discharged from the nozzle.

The electric-mechanic conversion system utilizes a property of a piezoelectric device deformed upon reception of a pulsated electric signal, in which a pressure is applied to a space where the material is stored via a flexible substance by deformation of a piezoelectric device and hence the material is pushed out from the space and discharged from the nozzle. The electric-thermal conversion system is a process of vaporizing the material rapidly by a heater provided in the space in which the material is stored to generate bubbles, and allows the material in the space to be discharged by the pressure of the bubbles. The electrostatic aspiration system is a process of applying a slight pressure in the space in which the material is stored to form a meniscus of material at the nozzle, and in this state, applying electrostatic attraction to draw out the material. There are also other applicable technologies such as a system of utilizing a variation of the viscosity of fluid due to the electric field, or a system of injecting by jump spark.

The piezoelectric liquid drop discharging process performed in the present embodiment has advantages in that waste of material is small and a desired amount of material can be disposed at desired positions accurately. The amount of one drop of a liquid-state material (fluid) to be discharged in the liquid drop discharging process is, for example, 1 to 300 nanograms.

Figure 3:
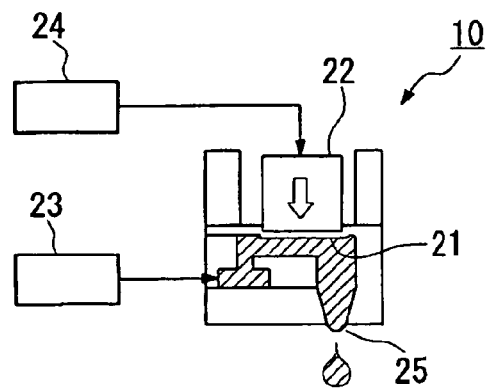
FIG. 3 is an explanatory drawing showing the principle of discharge of liquid member by a piezoelectric system.

FIG. 3 is an explanatory drawing showing the principle of discharge of liquid material through a piezoelectric liquid drop discharging head 10.

In FIG. 3, a piezoelectric device 22 is disposed adjacent to a liquid chamber 21 for storing the liquid material (ink for wiring pattern). The liquid chamber 21 receives a supply of liquid material via a liquid material feed system 23 including a material tank for storing the liquid material. The piezoelectric device 22 is connected to a driving circuit 24, and when a voltage is applied to the piezoelectric device 22 via the driving circuit 24, the piezoelectric device 22 is deformed, and hence the liquid chamber 21 is deformed, whereby the liquid material is discharged from a nozzle 25. In this case, by changing the value of applied voltage, the amount of deformation of the piezoelectric device 22 is controlled. Also, by changing the frequency of applied voltage, the speed of deformation of the piezoelectric device 22 is controlled. Since liquid drop discharge according to the piezoelectric system has an advantage in that constitution of the material is hardly affected because no heat is applied to the material.

In the present embodiment, liquid drops of the dispersion liquid are discharged from the liquid drop discharging head 10 and dropped on the plate where the wiring is to be formed. At this time, it is necessary to control the extent of overlapping of liquid drops discharged continuously so as not to generate a liquid pool (bulge). It is also possible to employ such a discharging process in which a plurality of liquid drops are discharged apart from each other so as not to come into contact with each other in the first discharging operation, and the remaining portion is filled in the second and subsequent discharging operations.

After the liquid drops have discharged, a drying process is performed as needed in order to remove the dispersion medium. The drying process can also be performed using, for example, a hot plate or an electric furnace for heating a plate W as in the normal process, and also by lamp annealing. Although the light source used for the lamp annealing is not specifically limited, an infrared lamp, a xenon lamp, a YAG laser, an argon laser, a carbon dioxide laser, and an excimer laser such as XeF, XeCl, XeBr, KrF, KrCl, ArF, or ArCl may be used as a light source. Though the light source generally used here is one having an output between 10 W and 5000 W inclusive, the output between 100 W and 1000 W is sufficient in the present embodiment.

Process of Heat Treatment/Optical Treatment

The dried film after the discharging process needs to be removed with the dispersion medium completely in order to achieve good electric contact between the fine particles. When the coating agent such as organic substances is applied on the surface of conductive fine particles for improving its dispersion property, this coating agent also has to be removed. Therefore, heat treatment and/or optical treatment are performed on the plate after the discharging process.

Normally, the heat treatment and/or the optical treatment are performed in ambient atmosphere. However, it can be performed in an inactive gas atmosphere, such as nitrogen, argon, and helium as needed. The treatment temperature for the heat treatment and/or the optical treatment is selected as needed considering the boiling point (steam pressure) of the dispersion medium, the type or the pressure of atmospheric gas, thermal behavior of the fine particles, such as the dispersion property or the oxidizing property, the presence or the amount of coating agent, or the heat-resistant temperature of the base material.

For example, in order to remove the coating agent formed of an organic substance, it is necessary to bake at about 300° C. When a plate of plastic, for example, is used, it is preferable to perform at a temperature between the room temperature and 100° C. inclusive.

The heat treatment and/or the optical treatment can be performed by the hot plate or the electric furnace, which are normally used, and also by lamp annealing. Although the light source used for lamp annealing is not specifically limited, an infrared lamp, the xenon lamp, the YAG laser, the argon laser, the carbon dioxide laser, and the excimer laser such as XeF, XeCl, XeBr, KrF, KrCl, ArF, or ArCl may be used as a light source. Though the light source generally used here is one having the output between 10 W and 5000 W inclusive, the output between 100 W and 1000 W is sufficient in the present embodiment.

With the process described above, on the dried film after the discharging process, electric contact between the fine particles is ensured, and hence the film is converted into the conductive film.

Since the conductive film formed by the present embodiment is formed on the plate in which the hydrophilic property, that is, the dot diameter and the contact angle are uniformly controlled, a thicker film of thinner lines is achieved.

Therefore, according to the present embodiment, the film thickness is large, which is advantageous for electric conduction, and hardly suffers from defects such as disconnection or short circuit. In addition, conductive film wiring which can be formed in minute detail is achieved.

As an example of a wiring pattern forming apparatus, a wiring forming device for embodying the above-described wiring pattern forming process will be described.

Figure 4:
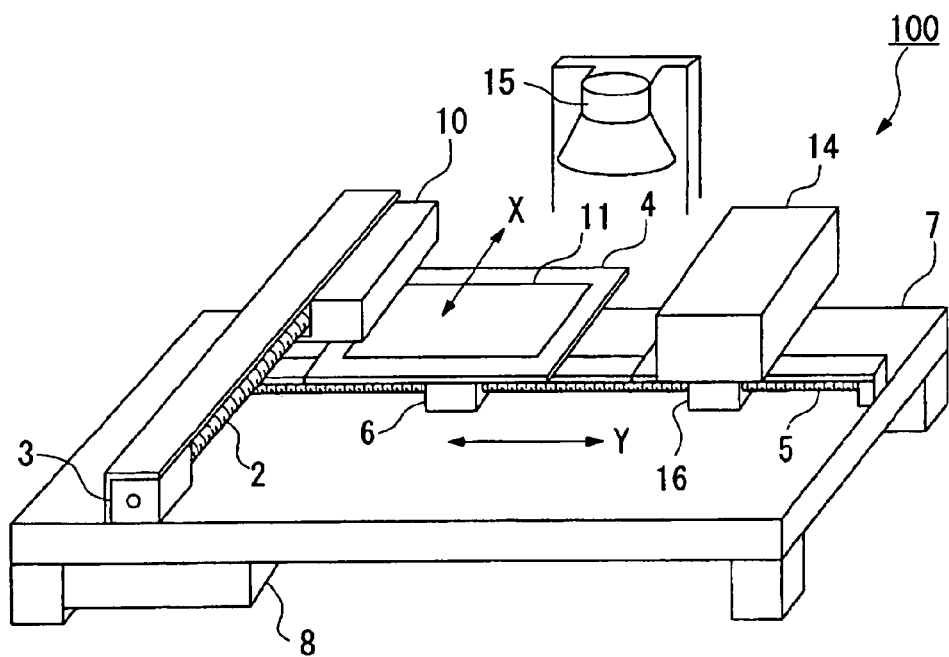
FIG. 4 is a general perspective view of a wiring forming device.

FIG. 4 is a general perspective view of the wiring forming device according to the present embodiment. As shown in FIG. 4, the wiring forming device 100 includes the liquid drop discharging head 10, an X-direction guiding shaft 2 for driving the liquid drop discharging head 10 in the X-direction, an X-direction driving motor 3 for rotating the X-direction guiding shaft 2, a bed plate 4 for placing the plate 11, a Y-direction guiding shaft 5 for driving the bed plate 4 in the Y-direction, a Y-direction driving motor 6 for rotating the Y-direction guiding shaft 5, a cleaning mechanism section 14, a heater 15, and a control unit 8 for generally controlling these components. The X-direction guiding shaft 2 and the Y-direction guiding shaft 5 are fixed on a base table 7, respectively. In FIG. 4, the liquid drop discharging head 10 is disposed at a right angle with respect to the direction of travel of the plate 11. However, the angle of the liquid drop discharging head 10 can be adjusted so as to intersect with the direction of travel of the plate 11. In this arrangement, the pitches of the nozzles can be adjusted by adjusting the angle of the liquid drop discharging head 10. A configuration in which the distance between the plate 11 and the nozzle surface can be adjusted as desired is also applicable.

The liquid drop discharging head 10 discharges liquid material of a dispersion liquid containing conductive fine particles from the nozzle (discharge port), and is fixed to the X-direction guiding shaft 2. The X-direction driving motor 3 is, for example, a stepping motor, and rotates the X-direction guiding shaft 2 when a driving pulse signal of the X-axis direction is supplied from the control unit 8. When the X-direction guiding shaft 2 rotates, the liquid drop discharging head 10 moves in the X-axis direction with respect to the base table 7.

As described above, the liquid drop discharging process may be various publicly known technologies such as a piezoelectric system, in which the piezoelectric device is used for allowing ink to be discharged, or a bubble system in which the liquid material is discharged by bubbles generated by heating the liquid material. Out of these two systems, the piezoelectric system does not apply heat to the liquid material, and hence it has an advantage in that constitution of the material is not affected.

The bed plate 4 is fixed to the Y-direction guiding shaft 5, and the Y-direction driving motors 6, 16 are connected to the Y-direction guiding shaft 5. The Y-direction driving motors 6, 16 are stepping motors and rotate the Y-direction guide shaft 5 when a driving pulse signal in the Y-axis direction is supplied from the control unit 8. The bed plate 4 moves in the Y-axis direction with respect to the base table 7 by the rotation of the Y-direction guiding shaft 5.

The cleaning mechanism section 14 cleans the liquid drop discharging head 10 and prevents the nozzle from clogging. The cleaning mechanism section 14 moves along the Y-direction guiding shaft 5 by the Y-direction driving motor 16 during the above-described cleaning operation.

The heater 15 provides heat treatment on the plate 11 using the heating means, such as lamp annealing or the like, promotes vaporization and drying of liquid discharged on the plate 11, and performs heat treatment for converting it into the conductive film.

In the wiring forming device 100 of the present embodiment, the liquid material is disposed on the plate 11 by moving the plate 11 and the liquid drop discharging head 10 with respect to each other via the X-direction driving motor 3 and/or the Y-direction driving motor 6 while discharging the liquid material from the liquid drop discharging head 10.

The amount of liquid drops discharged from each nozzle of the liquid drop discharging head 10 is controlled by a voltage supplied from the control unit 8 to the piezoelectric device.

The pitches of the liquid drops disposed on the plate 11 are controlled by the speed of the above-described relative movement and the discharging frequency from the liquid drop discharging head 10 (frequency of the driving voltage to the piezoelectric device).

The position to initiate dropping of liquid drops on the plate 11 is controlled by controlling the direction of the above-described relative movement and the timing of initiation of discharge of the liquid drops from the liquid drop discharging head 10 during the above-described relative movement.

Accordingly, the conductive film pattern for wiring described above is formed on the plate 11.

THIRD EMBODIMENT

Figure 5:
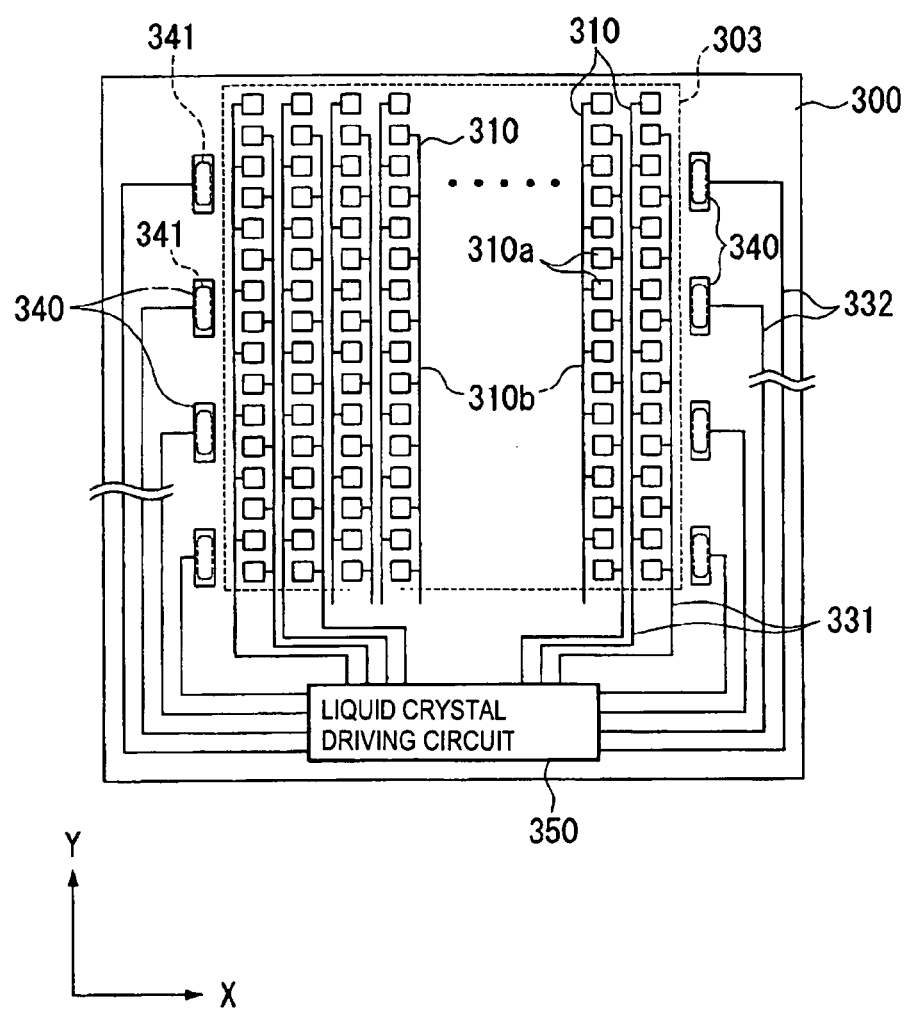
FIG. 5 is a plan view of the plate of a liquid crystal display device according to a third embodiment.

As a third embodiment, a liquid crystal display device, which is an example of an electro-optic device of the present invention will be described. FIG. 5 shows a plan layout of a signal electrode on a first plate of the liquid crystal display device according to the present embodiment. The liquid crystal display device according to the present embodiment generally includes the first plate, a second plate (not shown) provided with a scanning electrode and so on, and liquid crystal (not shown) encapsulated between the first plate and the second plate.

As shown in FIG. 5, a plurality of signal electrodes 310 . . . are provided in a multiple matrix manner on a pixel area 303 on the first plate 300. In particular, each signal electrode 310 . . . includes a plurality of pixel electrode portions 310a . . . provided corresponding to each pixel, and signal wiring portions 310b . . . for connecting the pixel electrode portions 310a . . . in a multiple matrix manner, and extends in the Y-direction.

Reference numeral 350 designates a liquid crystal driving circuit including a single chip, and the liquid crystal driving circuit 350 and each signal wiring portion 310b are connected via first leader wirings 331 . . . at one end (lower end in the drawing).

Reference numerals 340 . . . designate vertical conducting terminals, and the vertical conducting terminals 340 . . . and the terminal provided on the second plate, not shown, are connected by the vertical conducting materials 341 . . . . The vertical conducting terminals 340 . . . and the liquid crystal driving circuit 350 are connected by the second leader wirings 332 . . . .

According to the present embodiment, the signal wiring portions 310b . . . provided on the first plate 300, the first leader wirings 331 . . . , the second leader wirings 332 . . . are formed by the wiring forming process according to the second embodiment respectively.

According to the liquid crystal display device of the present embodiment, the liquid crystal display device in which defects such as disconnection or short circuit of the respective wirings hardly occur, and downsizing and reduction of thickness are achieved.

Subsequently, another embodiment of the liquid crystal display device, which is the electro-optic device of the present invention, will be described.

Figure 6:
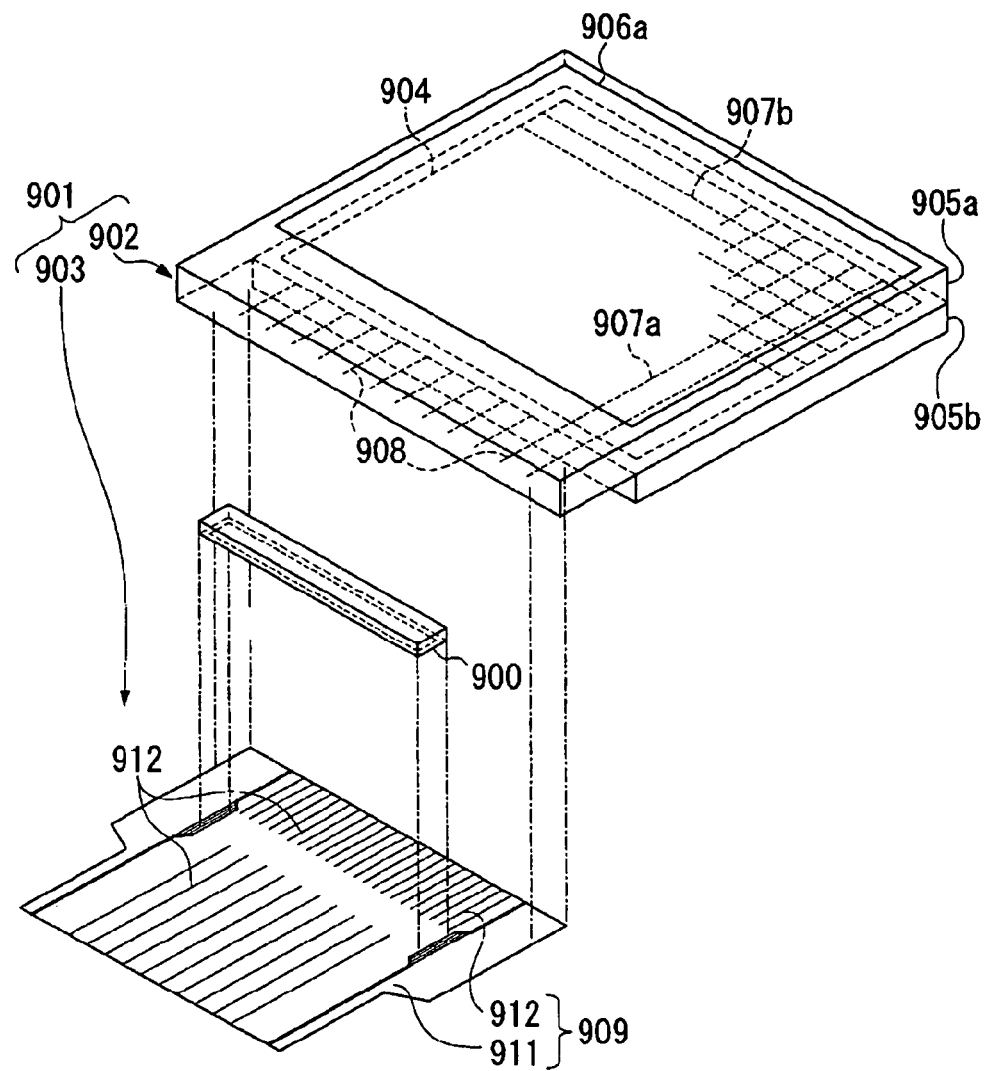
FIG. 6 is a drawing of another embodiment of the liquid crystal display device.

A liquid crystal display device (electro-optic device) 901 shown in FIG. 6 roughly includes a colored liquid crystal panel (electro-optical panel) 902, and a circuit plate 903 to be connected to the liquid crystal panel 902. When needed, an illumination device such as a back light or the like, or other accessories are provided on the liquid crystal panel 902.

The liquid crystal panel 902 includes a pair of plates 905a and 905b adhered by a sealing material 904, and liquid crystal is encapsulated in a gap defined between the plate 905b and the plate 905b, that is, in a cell gap. The plate 905a and the plate 905b are generally formed of translucent material, such as glass or synthetic resin. A deflecting plate 906a and a deflecting plate 906b are adhered on the outer surfaces of the plate 905a and the plate 905b. In FIG. 9, the deflecting plate 906b is not shown.

An electrode 907a is formed on the inner surface of the plate 905a, and an electrode 907b is formed on the inner surface of the plate 905b. These electrodes 907a, 907b are formed in stripes, characters, numbers or other appropriate patterns. The electrodes 907a, 907b are formed of translucent material, for example, ITO (Indium Tin Oxide). The plate 905a includes an overhanging portion overhanging toward the plate 905b, and a plurality of terminals 908 are formed on the overhanging portion. These terminals 908 are formed simultaneously with the electrode 907a when forming the electrode 907a on the plate 905a. Therefore, these terminals 908 are formed, for example, of ITO. These terminals 908 include the one extending from the electrode 907a, and the one connected to the electrode 907b via the conductive material (not shown).

A semiconductor device 900 as a liquid crystal driving IC is mounted at a predetermined position on a wiring plate 909 of the circuit plate 903. Though it is not shown in the drawing, a resistor, a condenser, or other chip components may be mounted at predetermined positions other than the portion to which the semiconductor device 900 is mounted. The wiring plate 909 is fabricated by patterning a metal film such as Cu formed on a base plate 911 having flexibility, such as polyimide, and forming a wiring pattern 912.

According to the present embodiment, the electrodes 907a, 907b of the liquid crystal panel 902 and the wiring pattern 912 in the circuit plate 903 are formed by the wiring forming process according to the second embodiment.

According to the liquid crystal display device of the present embodiment, a liquid crystal display device, in which defects such as disconnection or short circuit of the above-described respective wiring hardly occur, and downsizing and reduction in thickness are possible, is obtained.

While the example shown above is a passive-type liquid crystal panel, an active matrix type liquid crystal panel is also applicable. In other words, a thin film transistor (TFT) is formed on one of the plates, and a pixel electrode is formed for each TFT. Wirings for electrically connecting to the respective TFT (gate wiring, source wiring) can be formed by the inkjet technology as described above.

On the other hand, opposing electrodes and the like are formed on the opposed plate. The present invention can be applied also to the active matrix liquid crystal panel as described above.

FOURTH EMBODIMENT

Figure 7:
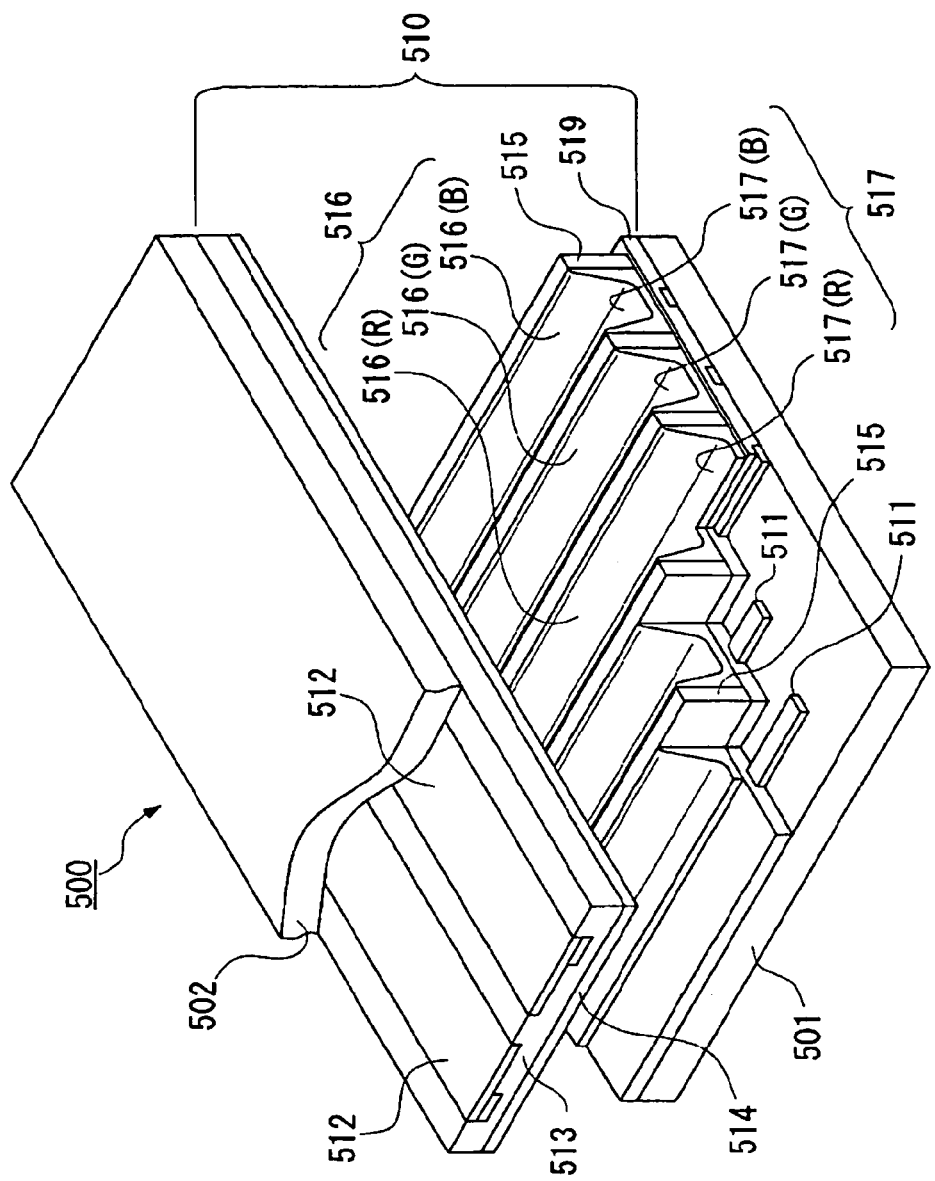
FIG. 7 is an exploded perspective view of a plasma-type display device according to a fourth embodiment.

As a fourth embodiment, a plasma-type display device, which is an example of the electro-optic device of the present invention will be described. FIG. 7 shows an exploded perspective view of a plasma-type display device 500 of the present embodiment.

The plasma-type display device 500 of the present embodiment generally includes a glass plate 501 and a glass plate 502 opposed to each other, and a discharge display unit 510 formed between these glass plates. The discharge display unit 510 includes a plurality of aggregated discharge chambers 516, and out of the plurality of discharge chambers 516, three discharge chambers 516; a red discharge chamber 516 (R), a green discharge chamber 516 (G), and a blue discharge chamber 516 (B); form a group and constitute one pixel.

Address electrodes 511 are formed into stripes at predetermined intervals on the upper surface of the (glass) plate 501, and a dielectric layer 519 is formed so as to cover the address electrodes 511 and the upper surface of the plate 501, and further, partition walls 515 are formed on the dielectric layer 519 between the address electrodes 511, 511 so as to extend along the respective address electrodes 511. The partition walls 515 are partitioned at predetermined intervals in the direction orthogonal to the address electrodes 511 at predetermined positions along the length thereof (not shown), and basically, rectangular areas partitioned by partition walls adjacent to the address electrodes 511 on the left and right sides thereof in the widthwise direction and the partition walls extending in the direction orthogonal to the address electrodes 511 are defined, and the discharge chambers 516 are formed so as to correspond to these rectangular areas. Three of these rectangular areas form a group, and constitute one pixel. Disposed within the rectangular areas partitioned by the partition walls 515 are fluorescent members 517. The fluorescent members 517 emit fluorescent light of any one of red, green, or blue. A red fluorescent member 517(R) is disposed on the bottom of the red discharge chamber 516(R), a green fluorescent member 517(G) is disposed on the bottom of the green discharge chamber 516(G), and a blue fluorescent member 517 (B) is disposed on the bottom of the blue discharge chamber 516(B), respectively.

Subsequently, on the side of the glass plate 502, there are provided a plurality of display electrodes 512 in the direction orthogonal to the aforementioned address electrodes 511 in stripes of predetermined intervals, a dielectric layer 513 is formed so as to cover the display electrodes 512, and a protective film 514, for example, of MgO is formed thereon.

The plate 501 and the glass plate 502 are bonded with each other with the address electrodes 511 . . . and the display electrodes 512 . . . orthogonally opposed, and the discharge chambers 516 are defined by discharging air from a space surrounded by the plate 501, the partition walls 515, and the protective film 514 formed on the side of the glass plate 502 and charging rare gas. The display electrode 512 on the glass plate 502 is formed two each for each discharge chamber 516.

The address electrodes 511 and the display electrodes 512 are connected to an AC power source, not shown, and electricity is supplied to each electrode, whereby the fluorescent members 517 in the discharge display unit 510 at required positions are excited, and thus emit light to achieve a color display.

According to the present embodiment, the address electrodes 511, and the display electrodes 512 are formed by the wiring forming process of the second embodiment.

According to the plasma-type display device of the present embodiment, a plasma-type display device, in which defects such as disconnection or short circuit of each electrode hardly occur, and downsizing and reduction in thickness are possible, is obtained.

FIFTH EMBODIMENT

Figure 8:
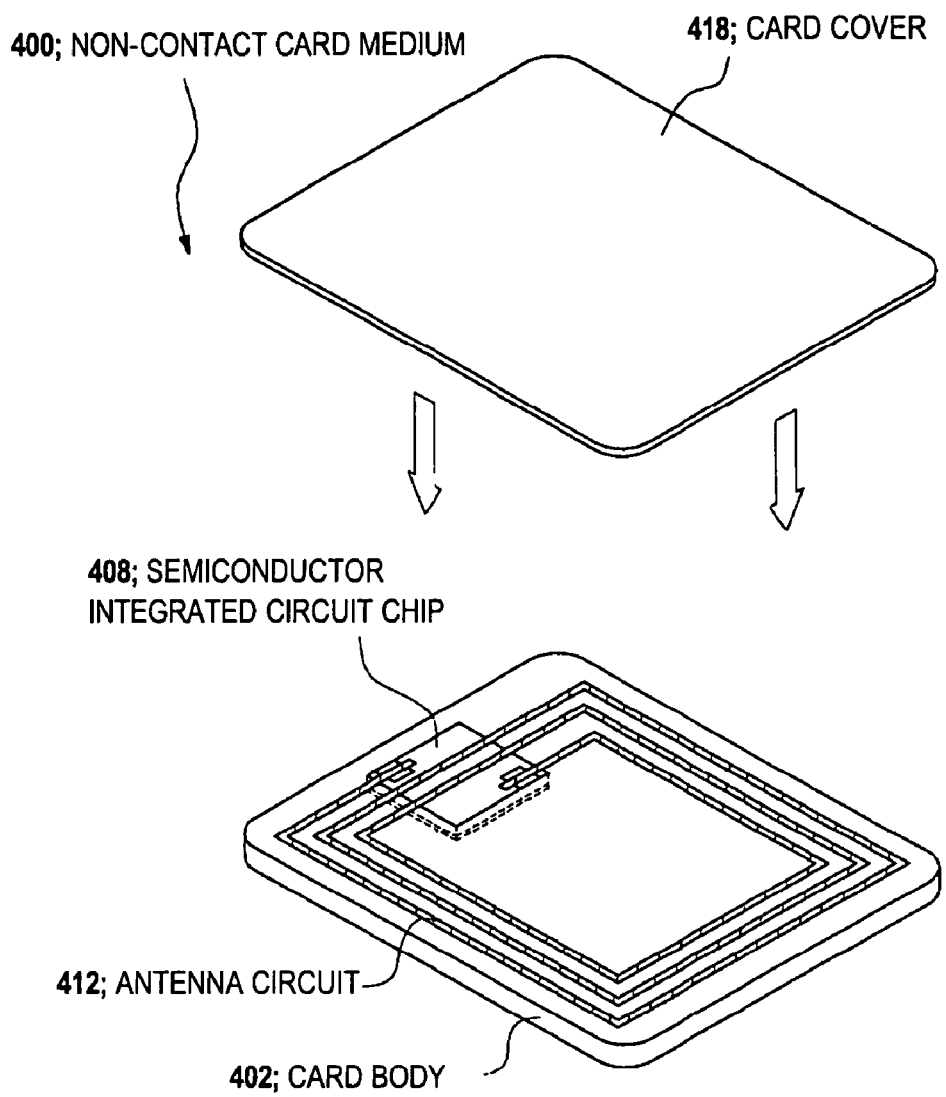
FIG. 8 is an exploded perspective view of a non-contact card medium according to a fifth embodiment.

As a fifth embodiment, an embodiment of a non-contact card medium of the present invention will be described. As shown in FIG. 8, the non-contact card medium (electronic equipment) 400 of the present embodiment is configure in such a manner that a semiconductor integrated circuit chip 408 and an antenna circuit 412 are integrated in an enclosure including a card body 402 and a card cover 418, and at least one of electric supply and data transfer is performed by at least one of an outside transmitter, not shown, and electromagnetic wave or by electrostatic capacity bonding.

In the present embodiment, the antenna circuit 412 is formed by the wiring forming process according to the second embodiment.

According to the non-contact card medium of the present embodiment, a non-contact card medium in which defects such as disconnection or short circuit of the antenna circuit 412 hardly occur, and downsizing and reduction in thickness are possible, is obtained.

SIXTH EMBODIMENT

As a sixth embodiment, a field emission display (hereinafter, referred to as "FED", which is an electro-optic device provided with a field emission element (electricity emission element) will be described.

Figure 9B:
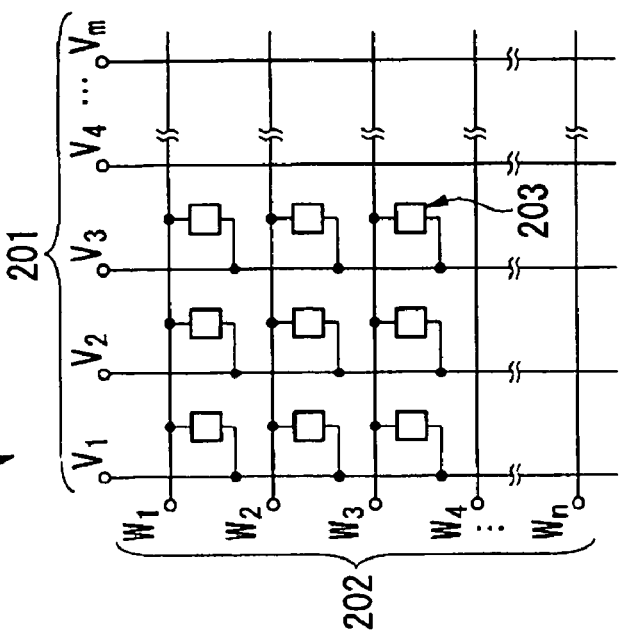
FIGS. 9A–C are explanatory drawings showing a field emission display (FED).
Figure 9A:
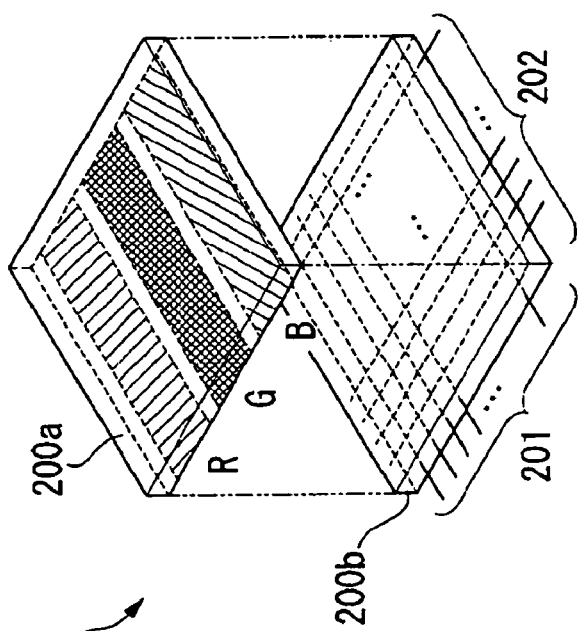
Figure 9C:
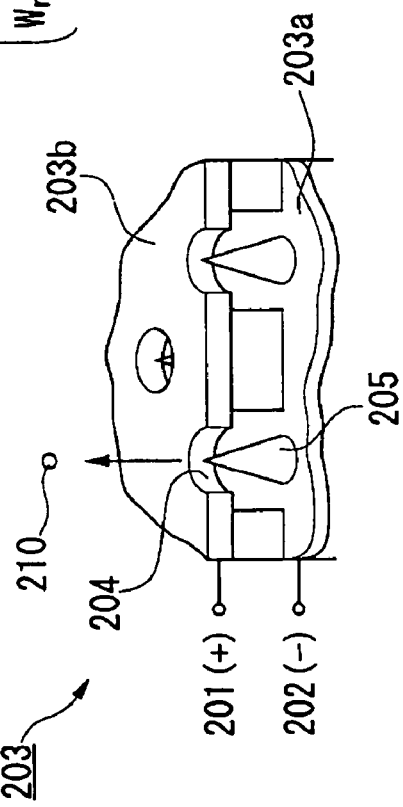
Figure 10:
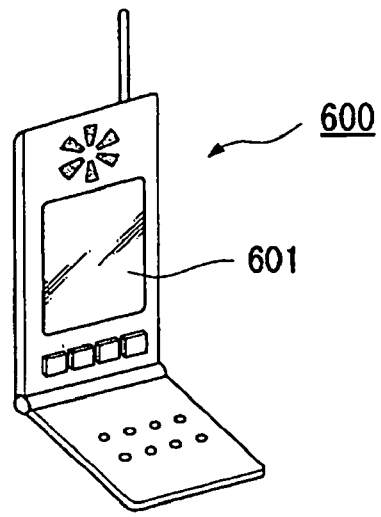
FIGS. 10A–C are drawings showing a detailed example of electronic equipment according to the present invention.
Figure 10:
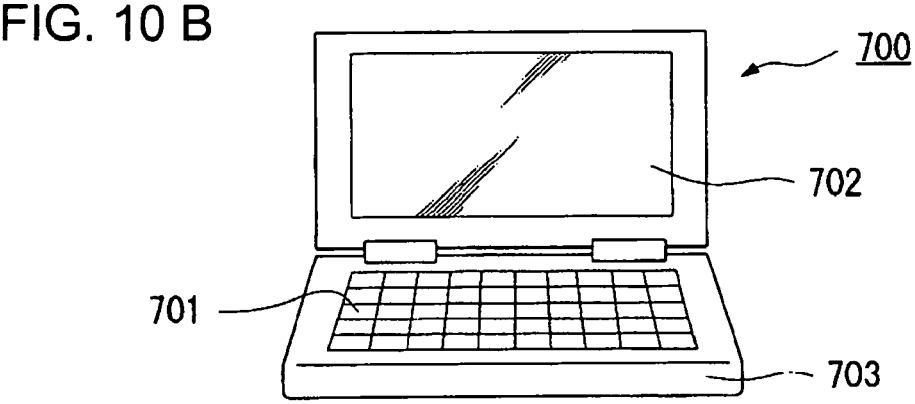
Figure 10:
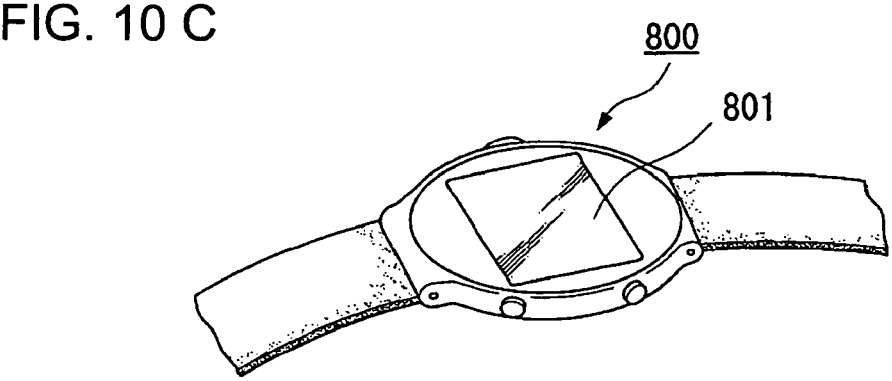

FIGS. 9A–C are explanatory drawings showing the FED. Fig. 9(a) is a general block diagram showing the layout of a cathode plate and an anode plate, which constitute the FED. FIG. 9(b) is a schematic block diagram of the driving circuit provided on the cathode plate of the FED. FIG. 9(c) is a perspective view showing a principal portion of the cathode plate.

As shown in FIG. 9(a), the FED (electro-optic device) 200 includes the cathode plate 200a and the anode plate 200b disposed so as to oppose to each other. The cathode plate 200a includes, as shown in FIG. 9(b), gate lines 201, emitter lines 202, and field emission element 203 connected to the gate liens 201 and the emitter lines 202. That is, so called simple matrix driving circuit is formed. The gate lines 201 are configured to receive gate signals V1, V2, . . . , Vm, and the emitter lines 202 are configured to receive emitter signals W1, W2, . . . , Wn. The anode plate 200b is provided with fluorescent members composed of RGB, and the fluorescent members have a property to emit light when subjected to electron.

As shown in FIG. 9(c), the field emission element 203 includes emitter electrodes 203a connected to the emitter lines 202, and gate electrodes 203b connected to the gate lines 201. Furthermore, the emitter electrode 203a is provided with projections called emitter tips 205 tapered from the emitter electrode 203a toward the gate electrode 203b. The gate electrode 203b is formed with holes 204 at the positions corresponding to the emitter tips 205, so that the extremities of the emitter tips 205 are placed in the holes 204.

In the FED 200 constituted as described above, a voltage is supplied between the emitter electrodes 203a and the gate electrodes 203b by controlling the gate signals V1, V2, . . . , Vm of the gate liens 201, and the emitter signals W1, W2, . . . , Wn of the emitter lines 202, then electrons 210 move from the emitter tips 205 into the holes 204 by the action of electrolyzation, and the electrons 210 is emitted from the extremities of the emitter tips 205. At this time, light is emitted when the electrons 210 and the fluorescent member of the anode plate 200b come into contact. Thus, desired driving of the FED 200 is achieved.

In the FED thus configured, for example, the emitter electrodes 203a, the emitter lines 202, and in addition, the gate electrodes 203b or the gate lines 201 are formed by the wiring forming process according to the second embodiment.

According to the FED of the present embodiment, an FED, in which defects such as disconnection or short circuit of the wirings hardly occur, and downsizing and reduction in thickness is possible, is obtained.

SEVENTH EMBODIMENT

As a seventh embodiment, detailed examples of electronic equipment of the present invention will be described.

FIG. 10(a) is a perspective view showing an example of a mobile telephone. In FIG. 10(a), reference numeral 600 designates a mobile telephone body, and reference numeral 601 designates a liquid crystal display unit provided with the liquid crystal display device according to the third embodiment.

FIG. 10(b) is a perspective view showing an example of a portable information processing device, such as a word processor, or a personal computer. In FIG. 10(b), reference numeral 700 designates an information processing device, reference numeral 701 designates an input device such as a keyboard, reference numeral 703 designates an information processing body, and reference numeral 702 designates a liquid crystal display unit provided with the liquid crystal display device according to the third embodiment.

FIG. 10(c) is a perspective view showing an example of watch type electronic equipment. In FIG. 10(c), reference numeral 800 designates a watch body, and reference numeral 801 designates a liquid crystal display unit provided with the liquid crystal display device of the third embodiment.

The electronic equipment shown in FIGS. 10(a)–(c) are provided with the liquid crystal display device of the embodiments described above, defects such as disconnection or short circuit of the wirings hardly occur, and downsizing and reduction in thickness is possible.

While electronic equipment of the present embodiment is provided with the liquid crystal display device, electronic equipment provided with other electro-optic devices such as an organic electroluminescence display device, a plasma-type display device, and an FED is also applicable.

While the preferred embodiments of the present invention have been described thus far referring to the attached drawings, it is to be understood that the present invention is not limited to those embodiments. The shape or combination of the respective components shown in the embodiments described above are simply shown as an example, and various modifications may be made based on deign requirements without departing the scope of the invention.

For example, the embodiments employ the configuration in which the plate is moved with respect to the mercury lamps, which are the sources of radiation (energy light). However, the invention is not limited thereto, and a configuration in which the mercury lamps are moved with respect to the plate may be employed. The process of relative movement between the radiation source and the plate is not limited to the swinging or reciprocating motion, a relative movement in one direction, or a relative rotation may be employed. In addition, a procedure in which the relative movement between the radiation sources and the plate is repeated while varying the speed of the relative movement between the plate and the radiation source by each movement or changing the levels of the plate and the radiation sources may also be applicable. The radiation source is not limited to the mercury lamp, and other radiation sources can be employed as long as radiation for providing the hydrophilic property to the surface of the plate can be irradiated.

What is claimed is:

1. A process of surface treatment comprising:
   a step of providing a hydrophobic property to a surface of a plate;
   a step of providing a hydrophilic property to the surface of the plate provided with the hydrophobic property by irradiating radiation thereon;
   a step of controlling variations in accumulated illumination intensity of the radiation on the surface of the plate to 20% or less; and
   a step of forming a conductive film on the surface of the plate by discharging a liquid material using an ink-jet.

2. A process of surface treatment according to claim 1, wherein variations in accumulated illumination intensity of the radiation on the surface of the plate are controlled to 15% or less.

3. A process of surface treatment according to claim 1, further comprising irradiating the radiation while relatively moving the plate with respect to a source of the radiation.

4. A process of surface treatment according to claim 3, further comprising moving the plate with respect to a plurality of arranged radiation sources in a direction of arrangement of the plurality of radiation sources.

5. A process of surface treatment according to claim 1, further comprising:
   a step of measuring illumination intensity of the radiation at a plurality of points on the surface of the plate and in a vicinity of the plate before providing the hydrophilic property; and
   a step of controlling irradiation of the radiation based on the accumulated illumination intensity of the radiation in the vicinity of the plate measured during the process of providing the hydrophilic property.

* * * * *